(12) United States Patent
Wissel et al.

(10) Patent No.: US 6,376,209 B2
(45) Date of Patent: *Apr. 23, 2002

(54) INCREASING THE FVII SENSITIVITY OF A THROMBOPLASTIN REAGENT

(75) Inventors: Thomas Wissel, Lahntal; Hermann Keuper, Wetter; Hubert Nettelhoff, Marburg; Heinz-Georg Kandel, Wetter; Reiner Muth; Michael Kraus, both of Marburg, all of (DE)

(73) Assignee: Dade Behring Marburg GmbH, Marburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,760

(22) Filed: May 15, 1998

(30) Foreign Application Priority Data

May 17, 1997 (DE) .......................... 197 20 853

(51) Int. Cl.$^7$ ............... C12Q 1/56; C12N 9/96; C12N 9/99; G01N 33/86; C01K 14/745
(52) U.S. Cl. ............... 435/13; 435/184; 435/188; 436/69; 530/384
(58) Field of Search ............... 435/13, 23, 184, 435/212, 188; 436/69, 80, 81, 120; 530/384, 389.3

(56) References Cited

U.S. PATENT DOCUMENTS

| | | | |
|---|---|---|---|
| 4,784,940 A | | 11/1988 | Gordon .................... 435/4 |
| 5,254,350 A | * | 10/1993 | Brown et al. ............. 424/570 |
| 5,314,695 A | * | 5/1994 | Brown ..................... 424/450 |
| 5,358,853 A | * | 10/1994 | Butler et al. ............. 435/13 |
| 5,504,193 A | * | 4/1996 | Hawkins et al. .......... 530/380 |
| 5,525,477 A | * | 6/1996 | Hassouna ................. 435/69 |
| 5,679,639 A | * | 10/1997 | Griffin et al. ............ 514/14 |
| 5,741,658 A | * | 4/1998 | Morrissey ................. 435/23 |

FOREIGN PATENT DOCUMENTS

| | | | | |
|---|---|---|---|---|
| CA | 2096888 | * | 11/1993 | ........... C12N/7/04 |
| EP | A 0 571 771 | | 4/1993 | |
| WO | WO 92/18539 | | 10/1992 | ........... C07K/15/06 |
| WO | WO 95/01571 | | 1/1995 | ........... G01N/33/86 |

OTHER PUBLICATIONS

Biemond et al., "Complete Inhibition of Endotoxin–Induced Coagulation Activation in Chimpanzees with a Monoclonal Fab Fragment Against Factor VII/VIIa," *Thorombosis and Haemostasis*, 73 (2), pp. 223–230 (1995).

Chabbat et al., "Aprotinin is a Competitive Inhibitor of the Factor VIIa–Tissue Factor Complex," *Thrombosis Research*, 71, pp. 205–215 (1993).

Broze et al., "Purification and Properties of Human Coagulation Factor VII," *The Journal of Biological Chemistry*, 255 (4), pp. 1242–1247 (Feb/1980).

Dalaker et al., "A Novel Form of Factor VII in Plasma From Men at Risk for Cardiovascular Disease," *British Journal of Haematology*, 61, pp. 315–322 (1985).

Sandset et al., "Chromogenic Substrate Assay of Extrinsic Pathway Inhibitor (EPI):Levels in the Normal Population and Relation to Cholesterol," *Blood Coagulation and Fibrinolysis*, 2, pp. 425–433 (1991).

Masahiro, "VII–TH A Factor Specific Antibody and Determination Thereof," Abstract only; PN 07209297. (Nov./1995).

Hiroshi, X–TH Factor Deficit Plasma, Abstract only; PN 59218960. (5/83).

W. B. Lawson et al., "Studies on the Inhibition of Human Thrombin: Effects of Plasma and Plasma Constituents" Folia Haematol. Leipzig 109 (1982) 1, S. 52–60.

S. E. Lind et al., "Oxidative Inactivation of Plasmin and Other Serine Proteases by Copper and Ascorbate" Blood, vol. 82 No. 5, pp. 1522–1531 (Sep./1993).

Amitava Dasgupta et al., "In vitro Lipid Peroxidation of Human Serum Catalyzed by Cupric Ion: Antioxidant Rather Than Prooxidant Role of Ascorbate", Life Sciences, vol. 50, pp. 875–882 (1992).

T. W. Barrowcliffe, et al., "The Effect of Fatty–acid Autoxidation Products on Blood Coagulation", Thrombos. Diathes. haemorrh., (1975) 33, 271.

* cited by examiner

Primary Examiner—M. P. Woodward
Assistant Examiner—Marjorie A. Moran
(74) *Attorney, Agent, or Firm*—Finnegan, Henderson, Farabow, Garrett & Dunner, L.L.P.

(57) ABSTRACT

The present invention relates to a process for increasing the FVII sensitivity of a thromboplastin reagent by means of heat treatment.

31 Claims, No Drawings

INCREASING THE FVII SENSITIVITY OF A THROMBOPLASTIN REAGENT

The present invention relates to a process for increasing the FVII (Factor VII) sensitivity of a thromboplastin reagent by means of heat treatment.

Quick's thromboplastin time (PT) is employed as a test for screening for a deficiency in coagulation factors in patient blood. The PT is also used to monitor therapy with oral anticoagulants. The preferred PT for normal blood donors is 10–14 seconds. The preferred PT for factor VII-deficient plasmas should be more than 60 seconds. The FVII sensitivity is therefore defined as the ratio of the coagulation time of the FVII-deficient plasma and the coagulation time for normal blood donors.

The invention describes a process for increasing the factor VII sensitivity of thromboplastin reagents by increasing the PT for factor VII-deficient plasmas without significantly altering the PT for normal plasmas.

Active thromboplastin induces coagulation in plasma and is composed of a lipid component and a protein component. The protein, i.e. tissue factor, is membrane-bound and is found in many different tissues. The binding between the protein and the lipid is based on hydrophobic interactions and is $Ca^{2+}$-independent. The protein moiety is composed of a glycoprotein having a molecular weight of 43–53 kDa. One molecule of tissue factor is able to bind to one molecule of FVII or FVIIa. The binding of FVII/FVIIa to tissue factor is $Ca^{2+}$-dependent. The complex composed of lipid, tissue factor and FVIIa cleaves FX to form FXa and thereby finally elicits coagulation by means of activating prothrombin.

The onset of coagulation in a plasma at from 10 to 14 sec. after adding a thromboplastin reagent indicates that the coagulation system is intact. An increase in the coagulation time points to an impairment. Impairments can occur as a result of the concentrations of one or more coagulation factors being too low. Thromboplastin reagents of varying origin frequently differ in their sensitivity for indicating the deficiency of particular factors. This can sometimes be due to the carry-over of small quantities of the factors to be determined into the reagent. Common methods for specifically removing small quantities of protein are, inter alia, immunoadsorption or, in the case of the vitamin K-dependent coagulation factors such as FII, VII, IX and X, barium sulfate adsorption (WO 90/05740). In the case of reagents of human origin, it is frequently only the sensitivity with regard to FVII which is inadequate.

Proteases, i.e. factors VIIa, IXa, Xa, XIa and XIIa, and plasma kallikrein and thrombin, are essential factors of the coagulation cascade.

Disadvantages of the previously described methods are, firstly, that FVII binds to tissue factor and the yield of tissue factor which is achieved by such an adsorption method is therefore reduced and, secondly, that both methods demand a substantial input of equipment and time, particularly on a production scale.

In the present invention, it is demonstrated that it is surprisingly possible, under defined conditions, to selectively inhibit the residual FVIIa activity of the reagent and consequently to arrive at the desired result in a simple manner without impairing the tissue factor or other factors of the coagulation cascade. The ratio, which is termed FVII sensitivity, of the coagulation time of the FVII-deficient plasma to the coagulation time of a normal plasma is preferably >4, particularly preferably >6 and very particularly preferably >10.

Factor VIIa possesses a protease activity and belongs to the serine protease class, as do the other coagulation factors IXa, Xa, XIa, XIIa, plasma kallikrein and thrombin. Another feature common to these coagulation factors is that they are initially present in zymogenic form and protein bonds have to be cleaved for their protease activity to be displayed.

A large number of protease inhibitors which at least inhibit the active forms of these zymogens, e.g. thrombin, have been described (W.B. Lawson et al., 1982, Folia Haematol. Leipzig 109 (1982) 1, pp. 52–60). They include sulfonyl fluorides, such as phenylmethylsulfonyl fluoride (PMSF), p-aminoethylbenzenesulfonyl fluoride (AEBSF) and 4-aminophenylmethanesulfonyl fluoride (p-APMSF), organofluorophosphates, such as diisopropyl fluorophosphate (DFP), chloromethyl ketones and also peptides, such as leupeptins or proteins of the serpin family, such as C1 inhibitor, antithrombin III and aprotinin.

The protease inhibitors suffer from the disadvantage that, in the PT, they inhibit the coagulation factors IXa, Xa, XIa, XIIa, plasma kallikrein and thrombin in the sample to be determined in addition to inhibiting the factor FVII or FVIIa which has been carried over. On this basis, they would prolong coagulation time and give a false impression of a pathological value. It is to be expected, therefore, that these inhibitors would not be suitable for being used in a PT reagent. Surprisingly, however, it is possible to employ these inhibitors under specific conditions without prolonging the coagulation times of the sample; however, the FVII sensitivity of the reagent is nevertheless improved.

Another option for inhibiting the enzymic activity of a protein is that of preparing specific antibodies which inhibit the active center of the protein. It is possible to obtain a variety of antibodies against coagulation factor VII, including at least one polyclonal antibody which inhibits the enzymic activity of FVII/FVIIa. Simply adding the antibody to a PT reagent would be disadvantageous since the antibody also inhibits the FVII/FVIIa of the sample. In the present invention, it is demonstrated that there is, surprisingly, a concentration range for adding the anti-FVII antibody in which the coagulation time of a normal plasma is not prolonged but that of an FVII-deficient plasma is prolonged markedly, such that the FVII sensitivity of the reagent is substantially increased.

It has also been previously reported that serine pro-teases can be oxidatively inhibited (S. E. Lind et al., 1993, Blood 82, 5 15522–1531). This method has the disadvantage that the fatty acids of the phospholipids can be oxidized in addition to the disadvantage that the coagulation cascade serine proteases in the sample are inhibited (Dasgupta, A. et al., Live Science 1992, 50, 875–882). The oxidation products which are produced in this connection likewise inhibit the PT (T. W. Barrowcliffe et al., 1975, Thrombos. Diathes. haemorrh. 33, 271).

Surprisingly, however, the oxidation process can be controlled such that it is possible to disregard the undesirable side reactions, i.e. while the coagulation time of normal plasmas is not prolonged, the FVII sensitivity of the reagent is improved. Suitable oxidizing agents are hypochlorite, hydrogen peroxide, permanganate and manganese dioxide. Many antioxidants, such as ascorbic acid, thiols, such as glutathione, acetyl cysteine, dithioerythreitol and tocopherols and tocopherol derivatives, such as di-tert-butyl-p-hydroxyanisole (BHA), di-tert-butyl-p-cresol (BHT), Trolox and propylgallate, are able to exert an oxidative effect in the presence of metal ions. The metal ions which catalyze the oxidation include, in particular, iron, copper and zinc. The metal-catalyzed oxidation is particularly suitable for inhibiting residual FVII/FVIIa activities.

The process of the present invention uses simple methods for heat-treating the tissue extract selectively; without thereby restricting ourselves to one particular reaction mechanism, it might be possible to explain the efficacy of the process on the basis that the specific heat treatment removes residual FVII/FVIIa activities. The heat treatment is advantageously carried out for a short time at high temperatures.

At low temperatures of between +40 and +60° C., inactivation of the FVII activities depends on a number of factors, inter alia the dimensions and the thermal conductivity of the vessel employed and the solution used, some of which cannot be controlled. The heating time can also vary widely. The heating temperature is advantageously between +65° C. and +160° C., preferably between +80° C. and 140° C., particularly preferably between +90 and +120° C.

So that the liquid which is supplied is heated to the relevant heating temperature in as short a time as possible and can then be cooled down again in a similarly short period of time, the apparatus in which the heating is carried out is expediently equipped with at least one connection for heating medium and at least one connection for cooling medium. The apparatus advantageously comprises three regions or sections: a heating section, in which the reagent is heated to the requisite temperature, a holding section, in which the reagent is held at this temperature for a specified time, and a cooling section in which the reagent is cooled down once again to a low temperature.

The construction of the heat-transfer apparatus should be such that the difference between the temperature to which the solution is heated and the temperature of the heating medium is as small as possible, as a consequence of which the product is spared to the greatest possible extent on account of the resulting low excess temperature of the walls which are in contact with the product.

Preference is given to a process for continuously heating for a short time, as described in EP-A 0 571 771 for virus inactivation.

The heating and/or cooling time should in each case be less than 30 seconds, preferably, however, less than 5 seconds. The holding time can be between 0.1 and 30 seconds, preferably, however, between 0.5 and 20 seconds.

Without restricting the invention to the example of human placenta extract, the following example demonstrates the inactivation of residual FVII/FVIIa activities by heating, as employed for a Behringwerke AG tissue thromboplastin-containing Quick reagent THROMBOREL S, Prod. No. OUHP placenta-thromboplastin. Preservatives, antioxidants, carbohydrates, proteins and amino acids, and combinations thereof, are advantageously added to the reagent as stabilizers. In the individual substance classes, the following compounds are particularly suitable:

Preservatives:

Mergal K9N (5-chlor-2-methylisothiazolin 3-on-2-methylisothiazolin 3-o), sodium azide phenol, amphotericin, gentamicin, piperacilin and ciprofloxacin.

Antioxidants:

Di-tert-butyl-p-hydroxyanisole (BHA), di-tert-butyl-p-cresol (BHT), spermine, propygallate, tocopherols, Trolox (6-hydroxy-2,5,7,8 tetramethyl-chroman-2-carboxylic acid, dithioerythreitol and glutathione.

Carbohydrates:

Trehalose, sucrose, Tylose (methylcellulose), mannitol, xanthan gum, phytagel, carrageenan and polyethylene glycol.

Proteins:

Lactoglobulin, lipoproteins and albumins, such as serum albumin, lactalbumin and ovalbumin.

Amino acids:

Acetylcysteine, acetylmethionine, glycine, lysine, histidine and serine.

The present invention also relates to processes for Increasing the FVII sensitivity of thromboplastin reagents, which comprise selectively inhibiting the residual FVII/FVIIa activity in the reagent, wherein a solution of these reagents is heated to greater than 65° C., and wherein the thromboplastin reagent is recombinant tissue thromboplastin or a biologically active variant of a tissue thromboplastin.

The following examples clarify the invention.

EXAMPLE 1

Step a)

1.25 ml of a stabilizing solution were added to THROMBOREL S Bulkware and the whole was made up to 10 ml. 1 ml of THROMBOREL (7° C.) was in each case added to 1.5 ml reaction tubes, which were then incubated at 560° C. in a water bath for different times and subsequently cooled on ice.

Step b)

Quick's thromboplastin time (PT) was then determined using a Schnitger & Gross as follows:

Heat reagents and tubes to 37° C.;

Introduce 100 gl of control plasma N or FVII-deficient plasma into the tubes;

Incubate for 1 min in the thermoblock;

Add 200 µl of thromboplastin and at the same time start the measuring operation; shake the tube briefly and place it in the measuring position of the Schnitger & Gross, and insert the electrode holder up to the limit stop;

Read off the coagulation time.

The read-off coagulation times are listed in Table 1:

TABLE 1

| | PT following thermal treatment | | | | | |
|---|---|---|---|---|---|---|
| | Standard human plasma (sec) | | | FVII-deficient plasma (sec) | | |
| min | 1. | 2. | MV | | | MV |
| Ref. | 10.4 | 10.5 | 10.5 | 28.4 | 27.9 | 28.2 |
| 1 | 10.5 | 10.5 | 10.5 | 28.4 | 27.9 | 28.2 |
| 2 | 10.6 | 10.6 | 10.6 | 29.1 | 29.6 | 29.4 |
| 3 | 10.5 | 10.9 | 10.7 | 33.0 | 33.0 | 33.0 |
| 4 | 10.8 | 10.9 | 10.9 | 34.9 | 34.0 | 34.5 |
| 5 | 11.0 | 11.1 | 11.1 | 36.6 | 36.5 | 36.6 |
| 10 | 12.0 | 11.9 | 12.0 | 45.4 | 44.5 | 45.0 |
| 15 | 14.5 | 15.0 | 14.8 | 116.0 | 116.4 | 116.2 |
| 20 | 15.5 | 16.0 | 15.8 | 128.0 | 126.0 | 127.0 |

EXAMPLE 2

THROMBOREL S Bulkware was heated, using a dwell time of 2.05 sec, to temperatures of from 60° C. to 80° C. (see Tab.2).

The coagulation time was determined as described in Example 1 step b).

TABLE 2

PT following short-time heating

| | Standard human plasma 100% (sec) | | | Standard human plasma 25% (sec) | | | FVII-deficient plasma 100% (sec) | | |
|---|---|---|---|---|---|---|---|---|---|
| | 1. | 2. | MV | 1. | 2. | MV | 1. | 2. | MV |
| Ref | 10.5 | 10.4 | 10.5 | 24 | 24 | 24.0 | 32.6 | 32.5 | 32.6 |
| 60° C. | 10.4 | 10.4 | 10.4 | 23.9 | 24.4 | 24.2 | 37.1 | 37 | 37.1 |
| 65° C. | 11 | 11 | 11.0 | 25 | 25.8 | 25.4 | 48 | 48.6 | 46.3 |
| 70° C. | 11 | 11 | 11.0 | 25.5 | 26 | 25.6 | 59.1 | 59.6 | 59.4 |
| 75° C. | 11.4 | 11.4 | 11.4 | 25.9 | 26.5 | 26.2 | 67.6 | 67.1 | 67.4 |
| 80° C. | 11.4 | 11.5 | 11.5 | 26.4 | 26.4 | 26.4 | 68.6 | 69.1 | 68.9 |

EXAMPLE 3

Thromborel S Bulkware was heated, using a dwell time of 0.5–2.05 sec, to temperatures of from 75° C. to 95° C. (see Tab. 3).

The coagulation time was determined as described in Example 1 step b).

TABLE 3

PT following short-time heating

| | Standard human plasma (sec) | | | FVII-deficient plasma (sec) | | |
|---|---|---|---|---|---|---|
| | 1. | 2. | MV | 1. | 2. | MV |
| 75° C. | 10.9 | 10.9 | 10.9 | 74.5 | 74.4 | 74.5 |
| 80° C. | 11.1 | 11.1 | 11.1 | 78 | 78.6 | 78.3 |
| 85° C. | 10.9 | 10.9 | 10.9 | 82.9 | 83.9 | 83.4 |
| 90° C. | 10.4 | 10.9 | 10.7 | 82.4 | 82.5 | 82.5 |
| 95° C. | 11 | 11.1 | 11.1 | 79.6 | 79.6 | 79.6 |
| 95° C. (1 sec) | 11 | 10.9 | 11 | 72 | 70.9 | 71.5 |
| 95° C. (0.5 sec) | 11 | 11 | 11 | 67.4 | 68 | 67.7 |
| Ref | 10.4 | 10.5 | 10.5 | 35.5 | 35.5 | 35.5 |

EXAMPLE 4

THROMBOREL S. prepared by the method described in the Examples 1a)–1b), was heated to temperatures of 65° C. and 75° C., respectively, using a dwell time of 2–16 sec (see Tab. 4). The coagulation time was determined as described in Example 1 step b).

TABLE 4

PT following short-time heating

| | Standard human plasma 100% (sec) | | | Standard human plasma 25% (sec) | | | FVII-deficient plasma 100% (sec) | | |
|---|---|---|---|---|---|---|---|---|---|
| | 1. | 2. | MV | 1. | 2. | MV | 1. | 2. | MV |
| Starting material | 10.5 | 10.4 | 10.5 | 26.9 | 26.5 | 26.7 | 33.6 | 33.5 | 33.6 |
| 2.0 sec RT | 10.5 | 10.5 | 10.5 | 26 | 26.4 | 26.2 | 33.1 | 33.5 | 33.3 |
| 15.5 sec 65° C. | 11.4 | 11.5 | 11.5 | 27.5 | 28.5 | 28.0 | 71.6 | 71.5 | 71.6 |
| 7.9 sec 65° C. | 11 | 10.9 | 11.0 | 27.5 | 27.4 | 27.5 | 58.1 | 59.1 | 58.6 |
| 4.0 sec 65° C. | 10.9 | 10.9 | 10.9 | 27.4 | 27 | 27.2 | 50 | 49.6 | 49.8 |
| 3.0 sec 65° C. | 10.9 | 11 | 11.0 | 27 | 26.5 | 26.8 | 48.6 | 48.6 | 48.6 |
| 2.0 sec 65° C. | 10.9 | 11 | 11.0 | 27.5 | 27.9 | 27.7 | 45.1 | 44.6 | 44.9 |
| 3.0 sec 75° C. | 11 | 11.4 | 11.2 | 28.5 | 28.9 | 28.7 | 71.6 | 72.6 | 72.1 |

EXAMPLE 5

Thromborel S, prepared by the method described in Examples 1a)–1b), was heated to a temperature of 90° C. using a dwell time of 3–18 sec (see Tab. 5).

The coagulation time was determined as described in Example 1 step b).

TABLE 5

PT following short-time heating

|  | Standard human plasma (sec) | | | FVII-deficient plasma (sec) | | |
| --- | --- | --- | --- | --- | --- | --- |
|  | 1. | 2. | MV |  |  | MV |
| 3 sec | 13.5 | 13.5 | 13.5 | 101.5 | 102 | 101.8 |
| 6 sec | 13.5 | 13.4 | 13.5 | 106.5 | 110.5 | 108.5 |
| 9 sec | 13.6 | 13.6 | 13.6 | 114.6 | 115.1 | 114.9 |
| 12 sec | 13.5 | 13.5 | 13.5 | 124.9 | 125.4 | 125.2 |
| 15 sec | 13.4 | 13.9 | 13.7 | 127.4 | 128 | 127.7 |
| 18 sec | 13.6 | 13.7 | 13.7 | 131.1 | 132 | 131.6 |

EXAMPLE 6

Thromborel S Bulkware was heated to a temperature of 120° C. using a dwell time of from 0.5 to 1.5 sec. The coagulation time was determined with a Behring Coagulation Timer using the PT.sec Thromborel S method.

TABLE 6

PT following short-time heating at 120° C. TB-255

| Dwell time in sec | 0.5 sec | 1.0 sec | 1.5 sec |
| --- | --- | --- | --- |
|  | Coagulation time in sec | | |
| Standard human plasma | 11.1 | 11.2 | 11.2 |
| FVII-deficient plasma | 120.7 | 146.8 | 155 |

EXAMPLE 7

Thromborel S Bulkware was heated to a temperature of 85° C. using a dwell time of 3 sec. Commercially obtainable Thromborel S and heated Thromborel (TB-190) were compared with the aid of various samples. The coagulation time was determined as described in Example 1 step b).

Samples

| PT100 | Standard human plasma | Batch designation: 502556 (98% of st.) |
| --- | --- | --- |
| Ctrl. P | Control plasma P | Batch designation: 512628 |
| MACI | Marcumar plasma I. | Batch designation: 951201 |
| MACII | Marcumar plasma II. | Batch designation: 951202 |
| PATH-I | Pathoplasma I. | Batch designation: 502883 |
| PATH-II | Pathoplasma II. | Batch designation: 502973 |
| FVII | Factor VII-deficient plasma | Batch designation: 500756 |

1 IU/ml Hep: Standard human plasma supplemented with 1 IU of heparin/ml.

MAC-02 and MAC-03: Plasma pools from orally anticoagulated patients

50% FVII and 2% FVII: dilutions of FVII-deficient plasma in standard human plasma.

PT16.75: Standard human plasma diluted to 16.75% in physiological NaCl solution.

% of standard: % of the standard (estimate using the following relationship):

$$C_x = (PT_{16.75\%} - PT_{100\%})/(4.97*PT_x - 4*PT_{100\%} + PT_{16.75\%})$$

ISI: international sensitivity index:

PR: $PT_{(Marcumar\ plasma)}/PT_{(standard\ human\ plasma)}$ $ISI_k$: ISI of the calibrated reagent;

$ISI_x$: ISI of the uncalibrated reagent $ISI_k = ISI_x * \log(PR_x)/\log(PR_k)$

TABLE 7

PT following short-time heating

|  | Thromborel S | | | | TB-190 | | | |
| --- | --- | --- | --- | --- | --- | --- | --- | --- |
|  |  | % of st. | PR | INR |  | % of st. | PR | ISI |
| PT100 | 11.15 |  |  |  | 10.05 |  |  |  |
| PT16.75 | 41.9 |  |  |  | 46.2 |  |  |  |
| 1 IU/ml Hep. | 12.25 | 84.9% | 1.10 | 1.11 | 10.1 | 99.3% | 1.00 |  |
| MACI | 34.95 | 20.6% | 3.13 | 3.43 | 31.2 | 25.6% | 3.10 | 1.09 |
| MACII | 66 | 10.1% | 5.92 | 6.82 | 67.8 | 11.2% | 6.75 | 1.01 |
| MAC-02 | 42.2 | 16.6% | 3.78 | 4.21 | 39.9 | 19.6% | 3.97 | 1.04 |
| MAC-03 | 60.9 | 11.1% | 5.46 | 6.26 | 58.4 | 13.1% | 5.81 | 1.04 |
| PATH-I | 29.25 | 25.5% | 2.62 | 2.83 | 25.2 | 32.4% | 2.51 |  |
| PATH-II | 51.45 | 13.3% | 4.61 | 5.21 | 44.75 | 17.3% | 4.45 |  |
| Crtl. P | 21.2 | 38.1% | 1.90 | 2.00 | 20.8 | 40.4% | 2.07 |  |
| 50% FVII | 12.65 | 80.5% | 1.13 | 1.15 | 11.45 | 83.9% | 1.14 |  |
| 2% FVII | 31.1 | 23.7% | 2.79 | 3.03 | 39.45 | 19.8% | 3.93 |  |
| FVII | 47.75 | 14.5% | 4.28 | 4.81 | 138.5 | 5.4% | 13.78 |  |
|  | /ISI = 1.08 |  |  |  |  |  |  |  |

EXAMPLE 8 a)
Thromborel S Bulkware is short-time heated (temperature 95° C., dwell time 0.5 sec) and aliquots were then treated with different protease inhibitors (Table 8). The stabilizers were added after the samples had been incubated overnight The reference does not contain any inhibitor.

b)
Quick's thromboplastin time (PT) is then determined using a Schnitger & Gross as follows:

Heat reagents and tubes to 37° C.;
Introduce 100 µl of plasma into the tubes;
Incubate for 1 min in the thermoblock;
Add 200 µl of thromboplastin and at the same time start the measuring operation;
shake the tube briefly, place it in the measuring position of the Schnitger & Gross, and insert the electrode holder up to the limit stop;
Read off the coagulation time.

The read-off coagulation times are listed in Table 8:

Standard human plasma (Behring Diagnostics) having a coagulation activity of approx. 100%, a 1:4 dilution of the standard human plasma (StHPl) in physiological sodium chloride solution (25%) and an FVII-deficient plasma (FVII-MP, Behring Diagnostics) were employed as samples. The spread was calculated from the ratio of the coagulation times for the dilution of the StHPl and the StHPl, and the FVII sensitivity was calculated from the ratio of the coagulation times for FVII-MP and STHPL.

TABLE 8

| Protease inhibitors | Concentration | 100% Coagulation times in sec | Patho II | FVII-MP | Spread: Patho II/ 100% | FVII sens.: FVII-MP/ 100% |
|---|---|---|---|---|---|---|
| pa-PMSF | 0.01 mM | 10.6 | 22.3 | 144 | 2.1 | 13.6 |
| pa-PMSF | 0.025 mM | 10.6 | 21.8 | 147 | 2.1 | 13.8 |
| pa-PMSF | 0.05 mM | 10.6 | 22.2 | 161 | 2.1 | 15.2 |
| pa-PMSF | 0.1 mM | 10.7 | 21.7 | 172 | 2.0 | 16.1 |
| pa-PMSF | 0.5 mM | 10.8 | 23.i | 298 | 2.1 | 27.6 |
| PMSF | 1.5 mM | 10.7 | 21.9 | 259 | 2.0 | 24.2 |
| Leupeptin | 0.5 mg/l | 10.6 | 22.5 | 121 | 2.1 | 11.4 |
| Pepstatin | 0.7 mg/l | 10.6 | 21.6 | 115 | 2.0 | 10.9 |
| Antagosan | 100K IU/ml | 10.6 | 22.2 | 118 | 2.1 | 11.1 |
| Reference | | 10.7 | 21.4 | 135 | 2.0 | 12.6 |

EXAMPLE 9

Stabilizers were added to Thromborel S Bulkware according to Example 8a), which bulkware had been short-time heated at a temperature of 85° C. and using a dwell time of 3 sec. and different concentrations of the protease inhibitor diisopropyl fluorophosphate (DFP) were also added to some aliquots; the reference does not contain any inhibitor.

The coagulation time was determined using a Behring Coagulation Timer (PT.sec Thromborel S). Standard human plasma, the. control plasma Patho II (Behringwerke AG) and an FVII-deficient plasma were employed as samples. The spread was calculated from the ratio of the coagulation times of the Patho II and the StHPl, and the FVII sensitivity was calculated from the ratio of the coagulation times for FVII-MP and STHPL.

TABLE 9

| Protease inhibitors | Concentration | 100% Coagulation times in sec | Patho II | FVII-MP | Spread: Patho II/ 100% | FVII sens.: FVII-MP/ 100% |
|---|---|---|---|---|---|---|
| DFP | 1 mM | 10.0 | 41.9 | 389 | 4.2 | 38.9 |
| DFP | 0.33 mM | 9.9 | 40.2 | 331 | 4.1 | 33.5 |
| DFP | 0.1 mM | 9.9 | 40.7 | 213 | 4.1 | 21.6 |

EXAMPLE 10

Preparation of an Anti-FVII Antibody

The FVII immunizing antigen was isolated from human plasma. After having been adsorbed on aluminum hydroxide, the bound proteins were eluted with 0.3 M sodium phosphate, pH 7.4. Following a subsequent precipitation with 16% ethanol, the supernatant was precipitated once again with 25% ethanol and the sediment was purified further using AE cellulose. The adsorbed proteins were eluted with a solution which contains 3% sodium citrate, 0.15 M sodium chloride and 0.09% EDTA, pH 8.0. Following further purification by means of PVC electrophoresis and column chromatography using Sephadex-G 100, the pure FVII was then used for the immunization.

Sheep were immunized by standard methods and the anti-FVII antibody was isolated from the serum.

Thromborel S Bulkware according to Example 8a) was short-time heated to a temperature of 85° C. using a dwell time of 3 sec and additionally treated with different concentrations of the above-described polyclonal antibodies.

The coagulation time was determined using a Behring Coagulation Timer (PT.sec Thromborel S). Standard human plasma, the control plasma Patho II and an FVII-deficient plasma were employed as samples. The spread as calculated from the ratio of the coagulation times of the Patho II and the StHPl, and the FVII sensitivity was calculated from the ratio of the coagulation times for FVII-MP and STHPL.

TABLE 10

| Antibody | Concentration µg/ml | 100% | Patho II | FVII-MP | Spread: Patho II/ 100% | FVII sens.: FVII-MP/ 100% |
|---|---|---|---|---|---|---|
| | | Coagulation times in sec | | | | |
| AB | 6.25 | 10.1 | 42.3 | 400 | 4.2 | 39.8 |
| AB | 0.625 | 10.0 | 41.2 | 301 | 4.1 | 30.2 |
| AB | 0.0625 | 9.9 | 40.4 | 163 | 4.1 | 16.5 |
| Reference | 0 | 9.9 | 39.2 | 136 | 4.0 | 13.8 |

EXAMPLE 11

Thromborel S Bulkware according to Example 8a) was short-time heated to a temperature of 85° C. using a dwell time of 3 sec and additionally treated with ascorbic acid, ascorbic acid and iron, and also ascorbic acid and copper. The stabilizers were added after an incubation of from 1 to 6 hours.

The coagulation time was determined as described in Example 8b).

Standard human plasma, the control plasma Patho II and an FVII-deficient plasma were used as samples. The reagents were stored at 4° C. and 37° C. and the coagulation time was repeated after 7 and 14 days. The spread was calculated from the ratio of the coagulation times of the Patho II and the StHPl, and the FVII sensitivity was calculated from the ratio of the coagulation times for FVII-MP and the STHPL.

TABLE 11

| Sample: | | SHPL | | |
|---|---|---|---|---|
| | Concentrations in mM | | | |
| Ascorbic acid: | 0 | 1 | 1 | 1 |
| Fe(II)SO$_4$: | 0 | 0 | 0.01 | 0 |
| CuCl: | 0 | 0 | 0 | 0.01 |
| Stabilization: | after 6 h | after 6 h | after 1 h | after 6 h |
| Sample: 100% | | | | |
| 18 h/4° C. | 12.9 | 13.7 | 15 | 13.7 |
| 7 days: 4° C. | 12.9 | 14 | 15.9 | 13.8 |
| 7 days: 37° C. | 13.4 | 14.7 | 16.4 | 14.6 |
| 14 days: 4° C. | 12.9 | 14.1 | 16 | 13.9 |
| 14 days: 37° C. | 14.8 | 15.3 | 17.1 | 15.5 |
| Sample: FVII | | | | |
| 18 h/4° C. | 126.4 | 157.7 | 139.8 | 243.3 |
| 7 days: 4° C. | 118.B | 154.3 | 153.2 | 240.8 |
| 7 days: 37° C. | 114.7 | 181.1 | 167.5 | 261.7 |
| 14 days: 4° C. | 118.2 | 161.6 | 157.9 | 245.8 |
| 14 days: 37° C. | 120.2 | 195.8 | 179 | 258.1 |
| Sample: Patho II | | | | |
| 18 h/4° C. | 47.6 | 51.4 | 62.7 | 48.5 |
| 7 days: 4° C. | 46.6 | 51.3 | 64.2 | 48.2 |
| 7 days: 37° C. | 48.6 | 51.5 | 60.3 | 48.8 |
| 14 days: 4° C. | 46 | 51.1 | 64.2 | 48.1 |
| 14 days: 37° C. | 57 | 53.1 | 62 | 53.6 |
| FVII sens.: FVII/100% | | | | |
| 18 h/4° C. | 9.8 | 11.5 | 9.3 | 17.8 |
| 7 days: 4° C. | 9.2 | 11.0 | 9.6 | 17.4 |
| 7 days: 37° C. | 8.6 | 12.3 | 10.2 | 17.9 |
| 14 days: 4° C. | 9.2 | 11.5 | 9.9 | 17.7 |
| 14 days: 37° C. | 8.1 | 12.8 | 10.5 | 16.7 |
| Spread: Patho II/100% | | | | |
| 18 h/4° C. | 3.7 | 3.8 | 4.2 | 3.5 |
| 7 days: 4° C. | 3.6 | 3.7 | 4.0 | 3.5 |
| 7 days: 37° C. | 3.6 | 3.5 | 3.7 | 3.3 |

EXAMPLE 12

Thromborel S Bulkware according to Example 8a) was short-time heated to a temperature of 120° C. using a dwell time of 0.75 sec and adjusted to pH 7.5 with 0.16 mM sodium carbonate; different concentrations of H$_2$O$_2$ were then added and the mixtures were incubated at 37° C. for 90 min. Stabilizers and 6 mM acetylcysteine were added to the solutions. The pH value was adjusted to 6.5 and the coagulation time was determined according to Example 8b).

Standard human plasma, the control plasma and an FVII-deficient plasma were used as samples. The FVII sensitivity was calculated from the ratio of the coagulation times for FVII-MP and STHPL.

TABLE 12

| Concentration of H$_2$O$_2$ | Coagulation time in sec | | FVII-sens. |
|---|---|---|---|
| | 100% | FVII-MF | FVII-MP/100% |
| 0.3% | 15 | 156 | 10.4 |
| 0.03% | 11.5 | 143 | 12.4 |
| 0.003% | 11.4 | 139 | 12.2 |
| 0.0003% | 11.7 | 133 | 11.4 |
| 0.00003% | 11.9 | 132 | 11.1 |
| — | 11.9 | 131 | 11.0 |

EXAMPLE 13

Thromborel S Bulkware according to Example 8a) was short-time heated at a temperature of 120° C. using a dwell time of 0.75 sec and then adjusted to pH 7.5 with 0.16 mM sodium carbonate; different concentrations of chloramine T were subsequently added and the mixtures were incubated at 37° C. for 90 min. Stabilizers and 6 mM acetylcysteine were added to the solution. The pH value was adjusted to 6.5 and the coagulation time was determined using a Behring Coagulation Timer (PT.sec Thromborel S).

Standard human plasma, the control plasma Patho II and an FVII-deficient plasma were used as samples. The spread was calculated from the ratio of the coagulation times of the Patho II and the StHPl, and the FVII sensitivity was calculated from the ratio of the coagulation times for the FVII-MP and the STHPL.

TABLE 13

| Concentration of chloramine T | Coagulation time in sec | | | Spread Patho II/ | FVII-sens. FVII-MP/ |
|---|---|---|---|---|---|
| | 100% | Patho II | FV-MP | 100% | 100% |
| 0.1 mM | 13 | 38.2 | 177.4 | 2.9 | 13.6 |
| 0.01 mM | 11.7 | 34.7 | 141.6 | 3.0 | 12.1 |

TABLE 13-continued

| Concentration of chloramine T | Coagulation time in sec | | | Spread Patho II/ 100% | FVII-sens. FVII-MP/ 100% |
|---|---|---|---|---|---|
| | 100% Patho II | FV-MP | | | |
| 0.001 mM | 11.5 | 34.2 | 140.1 | 3.0 | 12.2 |
| — | 11.6 | 34.2 | 142 | 2.9 | 12.2 |

What is claimed is:

1. A process for increasing FVII (Factor VII) sensitivity of a thromboplastin reagent, without impairing the tissue factor or other factors of the coagulation cascade, which comprises selectively inhibiting residual FVII/FVIIa activity in the reagent, wherein a solution of the reagent is heated to greater than 80° C. and then cooled.

2. The process as claimed in claim 1, further comprising holding time of between 0.1 and 30 seconds.

3. The process as claimed in claim 1, further comprising holding time of between 0.5 and 20 seconds.

4. The process as claimed in claim 1, wherein the reagent is a solution of tissue thromboplastin of human origin.

5. The process as claimed in claim 1, wherein the reagent is a solution of a recombinant tissue thromboplastin.

6. The process as claimed in claim 1, wherein the reagent is a solution of a biologically active variant of a tissue thromboplastin.

7. The process as claimed in one of claims 1, 4, 5, and 6, wherein heating is carried out continuously wherein heating or cooling time is less than 30 seconds in a heat transfer apparatus having indirect heating.

8. The process as claimed in one of claims 1, 4, 5, and 6, wherein heating temperature is greater than 80° C. but less than or equal to 160° C.

9. The process as claimed in claim 8, wherein the heating or cooling time is less than 30 seconds.

10. The process as claimed in claim 8, wherein the heating temperature is between +85° C. and 140° C.

11. The process as claimed in claim 10, wherein heating or cooling time is less than 30 seconds.

12. The process as claimed in claim 1, wherein a serine protease inhibitor is added to the reagent.

13. The process as claimed in claim 12, wherein the protease inhibitor comprises phenylmethylsulfonyl fluoride (PMSF), p-arninoethylbenzenesulfonyI fluoride (AEBSF), 4-aminophenylmethanesulfonyl fluoride (p-APMSF) or organofluorophosphates, or combinations of these inhibitors.

14. The process as claimed in claim 13, wherein the organofluorophosphate is diisopropylfluorophosphate (DFP).

15. The process as claimed in claim 1, wherein an anti-FVII antibody is added to the reagent.

16. The process as claimed in claim 15, wherein the antibody is a polyclorial anti-FVII antibody.

17. The process as claimed in claim 1, wherein an oxidizing agent is added to the reagent.

18. The process as claimed in claim 14, wherein the oxidizing agent comprises chloramine T, hydrogen peroxide, ascorbic acid, or combinations thereof.

19. The process as claimed in claim 17, wherein oxidation is carried out in the presence of metals.

20. The process as claimed in claim 19, wherein the oxidation is carried out in the presence of a metal selected from the group consisting of iron, copper or zinc, or their mixtures.

21. The process as claimed in one of claims 12, to 15, 17, 19, wherein a solution of tissue thromboplastin of human origin is the thromboplastin reagent.

22. The process as claimed in one of claims 12, 15, 17, 19, wherein a solution of a recombinant tissue thromboplastin is the thromboplastin reagent.

23. The process as claimed in claims 12, 15, 17, 19, wherein a solution of a biologically active variant of a tissue thromboplastin is the thromboplastin reagent.

24. The process of claim 11, wherein a stabilizer is added to the solution.

25. The process as claimed in claim 24, wherein the stabilizer is selected from preservatives, antioxidants, carbohydrates, proteins, amino acids, and combinations thereof.

26. The process of claim 25, wherein the preservatives are methylisothiazolin, sodium azide, phenol, amphotericin, gentamicin, piperacillin, or ciprofloxacin.

27. The process of claim 25, wherein the antioxidants are di-tert-butyl-p-hydroxyanisole, di-tert-butyl-p-cresol, spremine, propylgallate, tocopherols, chroman-2-carboxylic acid, dithioerythreitol, or glutathione.

28. The process of claim 25, wherein the carbohydrates are trehalose, sucrose, methylcellulose, mannitol, xanthan gum, phytagel, carrageen, or polyethylene glycol.

29. The process of claim 25, wherein the amino acids are acetylcysteine, acetylmethionine, glycine, lysine, histadine, or serine.

30. The process of claim 25, wherein the proteins are lactoglobulin, lipoproteins, or albumins, lactalbumin and ovalbumnin.

31. The process of claim 30, wherein the albumins are serum albumin, lactalbumin, and ovalbumin.

* * * * *

UNITED STATES PATENT AND TRADEMARK OFFICE
CERTIFICATE OF CORRECTION

PATENT NO.     : 6,376,209 B2
DATED          : April 23, 2002
INVENTOR(S)    : Thomas Wissel et al.

It is certified that error appears in the above-identified patent and that said Letters Patent is hereby corrected as shown below:

Column 13,
Line 29, "continuously wherein" should read -- continuously, wherein --.
Line 44, "p-arninoethylbenzenesulfonyI" should read -- p-aminoethylbenzenesulfonyl --.

Column 14,
Line 4, "polyclorial" should read -- polyclonal --.
Line 16, before "15," delete "to".
Line 17, before "19," insert -- and --.
Line 19, before "19," insert -- and --.
Line 25, "claim 11" should read -- claim 1 --.
Line 46, "ovalbumnin" should read -- ovalbumin --.

Signed and Sealed this

Twenty-fourth Day of June, 2003

JAMES E. ROGAN
*Director of the United States Patent and Trademark Office*